(12) United States Patent
Chan et al.

(10) Patent No.: US 6,923,992 B2
(45) Date of Patent: Aug. 2, 2005

(54) ACTIVE COMPOUNDS OF BAO-JI-WAN FOR ANTI-DIARRHEA AND RELIEVING GASTROINTESTINAL SYMPTOMS

(75) Inventors: Hsiao Chang Chan, Shatin (HK); Jing Mei Song, Richmond, VA (US); Paul Pui-Hay But, Tai Po (HK); Yiu Wa Chung, Ma On Shan (HK)

(73) Assignee: The Chinese University of Hong Kong, Shatin (HK)

( * ) Notice: Subject to any disclaimer, the term of this patent is extended or adjusted under 35 U.S.C. 154(b) by 203 days.

(21) Appl. No.: 10/313,772

(22) Filed: Dec. 6, 2002

(65) Prior Publication Data

US 2003/0152657 A1 Aug. 14, 2003

Related U.S. Application Data

(60) Provisional application No. 60/339,752, filed on Dec. 17, 2001.

(51) Int. Cl.[7] .............................................. A61K 35/78
(52) U.S. Cl. ...................................... 424/770; 424/725
(58) Field of Search .................................. 424/770, 725

(56) References Cited

U.S. PATENT DOCUMENTS 5,447,719 A * 9/1995 Kamataki ................... 424/741
6,039,954 A * 3/2000 Yu et al. ..................... 424/740

FOREIGN PATENT DOCUMENTS

CN          1240662 A  *  1/2000  .......... A61K/35/78

OTHER PUBLICATIONS

Dharmananda, S.; "Magnolia Bark," Institute for Traditional Medicine, Portland, Oregan, website http://www.itmonline.org/arts/magnolia.htm; Mar. 2001.*

* cited by examiner

Primary Examiner—Susan Coe
Assistant Examiner—S. B. McCormick-Ewoldt
(74) Attorney, Agent, or Firm—Townsend and Townsend and Crew LLP

(57) ABSTRACT

The invention provides methods for treating medical conditions caused by abnormal chloride ion flux with compositions containing active ingredients isolated from the traditional Chinese medicine Bao-Ji-Wan (BJW). The compositions comprise any one, two, or three of the following: magnolol, honokiol, imperatorin, isoimperatorin or only magnolol, honokiol, imperatorin, isoimperatorin and a physiologically acceptable carrier. In preferred embodiments, the medical conditions include disorders of the gastrointestinal tract, such as diarrhea and constipation.

34 Claims, 5 Drawing Sheets

Fig. Effect of BJW on diarrhea-induced by $MgSO_4$ in rat
$P<0.05$  ## $P<0.01$ compared with normal group
* $P<0.05$, *** $P<0.01$ compared with model group

ACTIVE COMPOUNDS OF BAO-JI-WAN FOR ANTI-DIARRHEA AND RELIEVING GASTROINTESTINAL SYMPTOMS

CROSS-REFERENCES TO RELATED APPLICATIONS

The present application claims priority to U.S. Ser. No. 60/339,752, filed Dec. 17, 2001, herein incorporated by reference in its entirety.

STATEMENT AS TO RIGHTS TO INVENTIONS MADE UNDER FEDERALLY SPONSORED RESEARCH AND DEVELOPMENT

Not applicable.

FIELD OF THE INVENTION

This invention relates to methods of using pharmaceutical compositions containing active ingredients of the traditional Chinese medicine Bao-Ji-Wan (BJW) for treatment of conditions with abnormal chloride ion flux. In particular, the present invention is directed towards gastrointestinal conditions like diarrhea and constipation.

BACKGROUND OF THE INVENTION

Regulation of chloride ion flux across cellular membranes is critical to maintaining homeostasis across epithelial membranes. Abnormal chloride ($Cl^-$) ion flux can lead to several different pathophysiological conditions, including cystic fibrosis, polycystic kidney disease, etc. One of the most widespread diseases is diarrhea, in particular infectious secretory diarrhea, where chloride and water secretion are upregulated by cholera toxin or excessive prostaglandin secretion in response to inflammation. Of all enteric pathogens that produce diarrhea in humans, cholera toxin, which stimulates chloride ion and fluid secretion by permanently activating the enzyme adenylate cyclase and cAMP, induces the most rapidly fatal condition.

According to the WHO, diarrhea is one of the leading causes of death in the world, particularly in developing countries where bacterial contamination of food and water is widespread. The problem is especially severe in children and infants, with more than 5 million children under age of 5 dying annually from malnutrition, diarrhea, and dehydration. Most of the currently available antidiarrheal agents act as antiperistaltic agents to inhibit gastric motility and peristalsis, while some are adsorbents and antibacterial agents. None of these have been shown to inhibit electrolyte and fluid secretion which, in most severe cases, is the cause of diarrhea. Antiperistaltic agents may cause central nervous system side effects, as well as unwanted effects on the GI tract including nausea, vomiting and abdominal discomfort. Moreover, while quite a number of traditional Chinese medicines provide alternative treatments for diarrhea, their active ingredients are usually not defined and their mechanisms of action are not clear. Thus there is a need in the art for a therapeutic agent with known active ingredients which specifically modulates chloride and water secretion. The present invention fulfills this and other needs.

SUMMARY OF THE INVENTION

In one aspect the invention provides methods for treating a medical condition caused by abnormal chloride ion flux, the methods comprising the step of administering to a subject a therapeutically effective amount of a pharmaceutical composition consisting essentially of any one, two, or three members selected from the group consisting of: magnolol, honokiol, imperatorin, and isoimperatorin; and a physiologically acceptable carrier. In certain embodiments, the subject is a human.

In one embodiment, the medical condition is caused by increased chloride ion and water secretion, such as certain disorders of the gastrointestinal tract. The disorder can be diarrhea caused by a virus, bacterium (e.g., cholera toxin), a neuroendocrine tumor, a parasite, or HIV. The methods can also be used to treat other conditions caused by increased chloride ion and water secretion, including, but not limited to, polycystic kidney disease and inflammatory bowel disease.

In another embodiment, the disorder is caused by decreased chloride ion and water secretion, such as a certain disorders of the gastrointestinal tract (e.g., constipation) and cystic fibrosis.

In another aspect, the invention provides methods for treating a medical condition caused by abnormal chloride ion flux, the method comprising the step of administering to a subject a therapeutically effective amount of a pharmaceutical composition consisting of: magnolol, honokiol, imperatorin, and isoimperatorin; and a physiologically acceptable carrier.

In yet another aspect, the invention provides methods for treating diarrhea, the methods comprising the step of administering to a subject a therapeutically effective amount of a pharmaceutical composition consisting essentially of one, two, or three members selected from the group consisting of: magnolol, honokiol, imperatorin, and isoimperatorin; and a physiologically acceptable carrier.

In still yet another aspect, the invention provides methods for treating diarrhea, the methods comprising the step of administering to a subject a therapeutically effective amount of a pharmaceutical composition consisting only of: magnolol, honokiol, imperatorin, and isoimperatorin; and a physiologically acceptable carrier.

In another aspect, the invention provides methods of modulating chloride ion flux, the methods comprising the step of administering to a subject a therapeutically effective amount of a pharmaceutical composition consisting essentially of any one, two, or three members selected from the group consisting of: magnolol, honokiol, imperatorin, and isoimperatorin; and a physiologically acceptable carrier.

In another aspect, the invention provides methods for treating constipation. The methods comprise the step of administering to a subject a therapeutically effective amount of a pharmaceutical composition consisting essentially of or consisting of any one, two, or three members selected from the group consisting of: magnolol, honokiol, imperatorin, and isoimperatorin; and a physiologically acceptable carrier. The constipation can arise from conditions including, but are not limited to, gastrointestinal carcinoma, Behect's disease, primary or secondary enteric neuropathies, gastrointestinal dysfunction in Parkinson's disease, irritable bowel syndrome, chronic constipation, bowel dysfunction in Hirschsprung's disease, slow transit constipation, gastrointestinal dysfunction in Alzheimer's disease, or chronic opioid treatment.

DETAILED DESCRIPTION

Introduction

Figure 1:
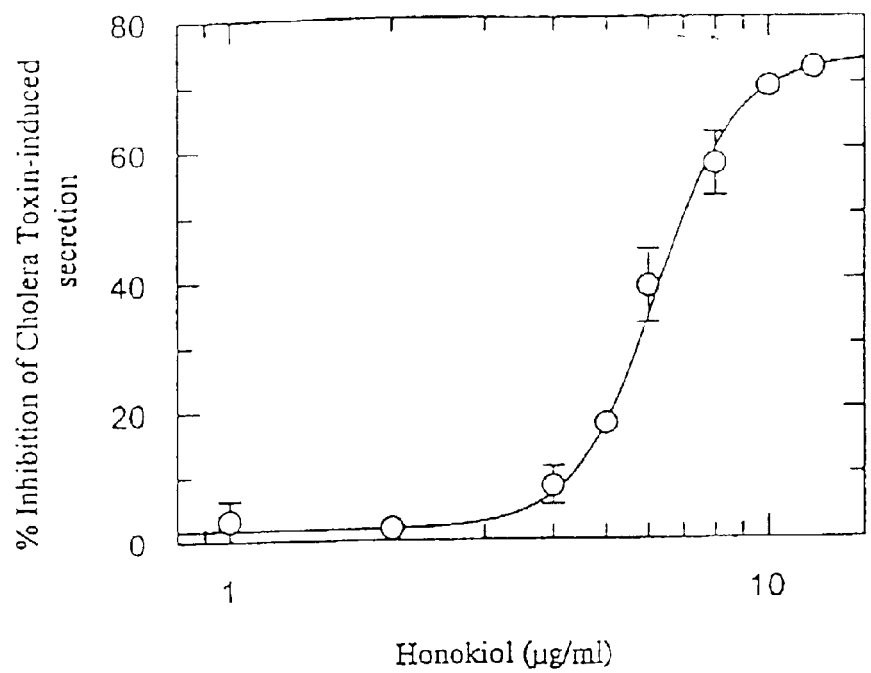
FIG. 1. Inhibition of cholera-induced and forskolin-induced chloride ion secretion by honokiol.
Figure 1:
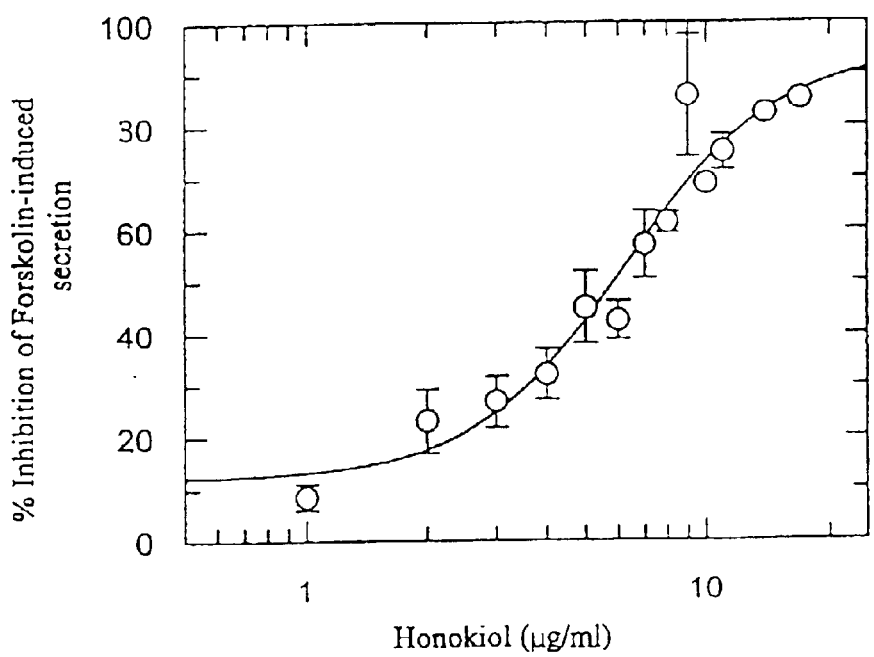

The present invention provides methods of using active compounds of a traditional Chinese medicine, Bao-Ji-Wan (BJW), also known as Po Chai Pill and Bao Ji Pill, which consists of more than ten herbs and is presently used as a broad-spectrum antidiarrheal agent and laxative.

Four active compounds, magnolol, honokiol, imperatorin, and isoimperatorin have now been isolated from BJW and shown individually to inhibit excessive cAMP-mediated chloride ion secretion and to stimulate secretion in the absence of hypersecretion. Isolation of these compounds and demonstration of efficacy for isolated compounds allows for formulation of pharmaceutical compositions with varying combinations of the active ingredients, each composition tailored to optimize desired effects and minimize side effects. In preferred embodiments, the invention comprises any one, two, or three of either magnolol, honokiol, imperatorin, or isoimperatorin. In alternative embodiments, the invention consists only of magnolol, honokiol, imperatorin, isoimperatorin, and a physiologically effective carrier.

As potent modulators of chloride ion flux, these compounds are particularly directed towards treatment of pathological conditions arising from abnormal chloride ion flux, including both conditions caused by increased chloride ion and water secretion, as well as those caused by decreased chloride ion and water secretion. In certain embodiments, the method is directed towards polycystic kidney disease, inflammatory bowel disease, cholera, cystic fibrosis, etc. Most preferably, the method is directed towards diseases of the gastrointestinal tract, including diarrhea and constipation. The diarrhea can be caused by a virus, a bacterium, a neuroendocrine tumor, a parasite, or HIV. The potent effect of these compounds on chloride and water secretion allows for the treatment of GI disorders due to a variety of causes without the concomitant nervous system side effects arising from antidiarrheal agents whose primary mode of action is inhibition of peristalsis.

In other embodiments, the compounds are directed towards treatment of other disorders of the gastrointestinal tract or diseases with symptoms that affect the gastrointestinal system. In certain instances these diseases/symptoms are caused by abnormal chloride flux, but in other instances they are caused by other factors. For example, the ability of compounds of this invention to inhibit water and chloride ion flux can be used to treat diarrheas regardless of the cause.

Both BJW and plant extracts containing a subset of the compounds of this invention have been shown to inhibit noninfectious diarrheas. In addition, the ability of compounds of this invention to stimulate water and chloride ion flux can be used to treat symptoms of numerous diseases with effects related to constipation, such as a gastrointestinal carcinoma, Behect's disease, primary or secondary enteric neuropathies, gastrointestinal dysfunction in Parkinson's disease, irritable bowel syndrome, chronic constipation, bowel dysfunction in Hirschsprung's disease, slow transit constipation, gastrointestinal dysfunction in Alzheimer's disease, and side effects of chronic opioid treatment.

In other aspects, this invention comprises combinations of the active ingredients with other therapeutically effective agents. The concept of combination therapy is well exploited in current medical practice. Treatment of a pathology by combining two or more agents that target the same pathogen or biochemical pathway sometimes results in greater efficacy and diminished side effects relative to the use of the therapeutically relevant dose of each agent alone. Preferably, the active ingredients are administered in combination with other agents which modulate chloride ion secretion or treat gastrointestinal disorders.

Definitions

As used herein, the following terms have these meanings ascribed to them unless specified otherwise.

Administration of a "therapeutically effective" amount of the compositions of the present invention is defined as an amount effective, at dosages and for periods of time necessary to achieve the desired result. The therapeutically effective amount of the compositions of the invention may vary according to factors such as disease state, age, gender, and the weight of the individual. Dosage regimens may be adjusted to provide the optimum therapeutic responses. For example, several divided doses may be administered daily or in one administration, over one or more days.

A "pharmaceutically acceptable salt" is an organic or inorganic salt that is suitable for administration to a subject, e.g., a mammal or a human.

A "physiologically acceptable carrier or diluent" is a vehicle that is suitable for administration to a mammal such as a human. Suitable diluents or carriers include sterile solutions such as saline, aqueous buffer solutions, glycerol, and the like.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A compound that is the predominant species present in a preparation is substantially purified. Particularly, it means that the compound is preferably at least 85% pure, more preferably at least 95% pure, and most preferably at least 99% pure.

"Abnormal chloride ion flux" refers to movement of chloride ions across the cell membrane in a manner which deviates from that occurring in normal healthy subjects. Chloride flux can be measured according to methodology well known to those of skill in the art. For example, the short-circuit current technique and flux measurement using either isotope or fluorescence.

A method of "treating" a medical condition in a subject refers to method of reducing or inhibiting symptoms, or hastening or providing a cure. Decreased symptoms of medical conditions can be measured by a number of methods, by using the methods described herein or using standard methods known to those of skill in the art. To examine the extent of reduction of symptoms, a subject (e.g., a rat) is treated with a potential modulator and is compared to control samples without the modulator.

Methods of Isolating or Synthesizing Compounds

The chemical formulas and structures of the compounds of this invention are disclosed in JP4368324 (magnolol and honokiol), JP5025008 (imperatorin and isoimperatorin), and JP9157166 (imperatorin and isoimperatorin).

The compositions of the invention comprising magnolol, honokiol, imperatorin, and isoimperatorin can be plant extracts, purified compounds or mixtures of compounds from plant extracts or de novo synthesized compounds that have the same or similar chemical structures as those found in plant extracts. Methods of preparing extracts are described herein and in the art, e.g., JP426403 ("Extraction of Magnolol from Magnolol-containing Plant"), for extraction for imperatorin, Garcia-Argaez et al., *Planta Med* 66(3):279–81 (2000), and for extraction for isoimperatorin, Yang et al., *J Chromatogr* 883(1–2) :67–73 (2000). Such extracts and compounds are also commercially available.

Assays for Testing Ability of Compounds to Alter Chloride Ion and Water Flux

The activity of the above described compounds can be tested according to the assays described herein. The ability of compounds to modulate fluid secretion can be assayed by a variety of in vitro and in vivo assay methods known to those of skill in the art. Preferably, fluid accumulation is induced by a stimulation of inflammation (e.g., using prostaglandins), either before or after administration of the compound. Fluid accumulation can be measured in the presence and absence of a compound (e.g., in grams fluid/ grams intestine) to determine the degree of inhibition. For a more detailed description of methods, see Robert et al., *Prostaglandins* 11(5):809–28 (1976); Rani et al., *J Ethnopharmacology* 68(1–3):315–9 (1999); Kisloff et al., *Gastroenterology* 72(3):462–8 (1977); Cunha Ferreira et al., *Acta Paediatr* 81(1):46–50 (1992).

The ability of compounds to modulate chloride ion secretion can be assayed by a variety of in vitro and in vivo assay methods known to those of skill in the art. Preferably, chloride ion secretion is induced by stimulating a chloride ion-secreting mammalian cell line (e.g., T84, a human colonic cell line) with any agent that elevates cAMP levels (e.g., forskolin or cholera toxin) in the absence and presence of test compound. Levels of chloride secretion can be measured by any method known to those of skill in the art, but preferably by the short-circuit current technique or flux measurement using isotope or fluorescence (Donowitz M et al., *Annu. Rev. Physiol* 48: 135–150 (1986); McCabe RD et al., *Am J Physiol* 247(4 Pt 1):G411–8 (1984); Foster E S et al. *J Clin Invest* 77:228–235 (1986); Chao et al., *J Membr Biol*113(3):193–202 (1990); Fondacaro et al., *J Pharmacol Exp Ther* 247(2):481–6 (1988)).

The in vivo effects of these compounds can be determined using animal models for diarrhea or constipation known to those of skill in the art. Preferably, diarrhea is induced in mammals (e.g., rats) by magnesium sulfate or DaHuang, the mammals are treated with the compounds, and the effect determined by comparison of intestinal transit and diarrhea, measured by methods known the those of skill in the art, e.g., Fiocchi et al., *Life Sci* 31:2221–3 (1982); Ozaki et al., *Jpn J Pharmacol* 80: 93–96 (1999). Constipation can be induced in mammals by morphine, verapamil, atropine, or amitriptyline (Tsusumi et al., *Biol Pharm Bull* 23(5):657–9 (2000); Bianchi et al., *Gastroenterology* 85(4):852–8 (1983); Calignano et al., *Gen Pharmacol* 23(4):753–6 (1992)).

Pharmaceutical Compositions and Administration

In certain embodiments, the pharmaceutical compositions of this invention comprise any one, two, three, or four of the following compounds: magnolol, honokiol, imperatorin, and isoimperatorin. In particularly preferred embodiments, the compositions comprises magnolol alone, magnolol in combination with any of the other compounds (honokiol, imperatorin, and isoimperatorin), or all four compounds together (magnolol, honokiol, imperatorin, and isoimperatorin).

Physiologically acceptable carriers are determined in part by the particular composition being administered (e.g., composition of active ingredients of BJW), as well as by the particular method used to administer the composition. Accordingly, there are a wide variety of suitable formulations of pharmaceutical compositions of the present invention (see, e.g., *Remington's Pharmaceutical Sciences*, $17^{th}$ ed., 1989). Administration can be in any convenient manner, e.g., by injection, oral administration, inhalation, transdermal application, or rectal administration. Dosages and administration may be determined using the in vivo and in vitro models provided herein.

Formulations suitable for oral administration can consist of (a) liquid solutions, such as an effective amount of an active ingredient of BJW suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The formulations can be presented in unit-dose or multi-dose sealed containers, such as ampules and vials. The dose administered to a patient, in the context of the present invention should be sufficient to effect a beneficial therapeutic response in the patient over time. The dose will be determined by the efficacy of the particular composition employed and the condition of the patient, as well as the body weight or surface area of the patient to be treated. The size of the dose also will be determined by the existence, nature, and extent of any adverse side effects that accompany the administration of a particular composition in a particular patient.

In determining the effective amount of the composition to be administered in the treatment or prophylaxis of conditions, the physician evaluates circulating plasma levels of the composition, composition toxicities, progression of the disease, and the production of anti-composition antibodies. In general, the dose equivalent is about 1 mg/kg body weight, wherein the mixture of compounds is in any ratio.

For administration, compounds of the present invention can be administered at a rate determined by the LD-50 of the composition, and the side effects of the composition at various concentrations, as applied to the mass and overall health of the patient. Administration can be accomplished via single or divided doses.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are offered to illustrate, but not to limit the claimed invention.

Example 1

This example illustrates the ability of BJW and its active components, magnolol, honokiol and imperatorin, to inhibit $PGE_2$-induced fluid accumulation in rats. Sprague-Dawley rats of either sex, in groups of 8 animals, weighing between 220 and 250 g were used. A modified $PGE_2$-induced enteropooling assay (Robert et al., *Prostaglandins* 11(5):809–28 (1976)) was used. The test drugs or vehicle were administrated intergastrically to rats 60 min before the administration of $PGE_2$ (100 µg/kg, i.g.). BJW was administered (i.g. 1.6 g/kg, 2× of recommended human dosage) once daily for two days before treatment with $PGE_2$. Fluid accumulation/g weight of intestine was measured and % inhibition was calculated as shown in Table 1. The test shows that BJW and its active components have an inhibitory effect on $PGE_2$-induced fluid accumulation. The effect of BJW and magnolol is significantly more potent than that of a popular commercially available antidiarrheal agent loperamide, at a dose 2× of the recommended human dosage.

TABLE 1

Effects of BJW and said components on fluid accumulation induced by $PGE_2$

| Group | dose | Fluid accumulation ratio (FA) (fluid g/g intestine) | Inhibition of secretion (%) |
| --- | --- | --- | --- |
| Normal | vehicle | 2.47 ± 0.13 | |
| $PGE_2$ Model | 100 µg/kg | 12.87 ± 2.03### | |
| BJW | 1.6 g/kg | 3.10 ± 0.35*** | 94 |
| Honokiol | 2 mg/kg | 7.06 ± 1.18* | 56 |
| Magnolol | 2 mg/kg | 3.28 ± 0.32*** | 92 |
| Imperatorin | 2 mg/kg | 8.87 ± 1.93 | 39 |
| Loperamide | 2 mg/kg | 5.09 ± 1.40* | 75 |

$p < 0.01$ compared with normal group
$P < 0.05$, *** $P < 0.01$ compared with model group
% inhibition of secretion = $(FA_{model} - FA_{test})/(FA_{model} - FA_{normal}) \times 100\%$

Example 2

Figure 2:
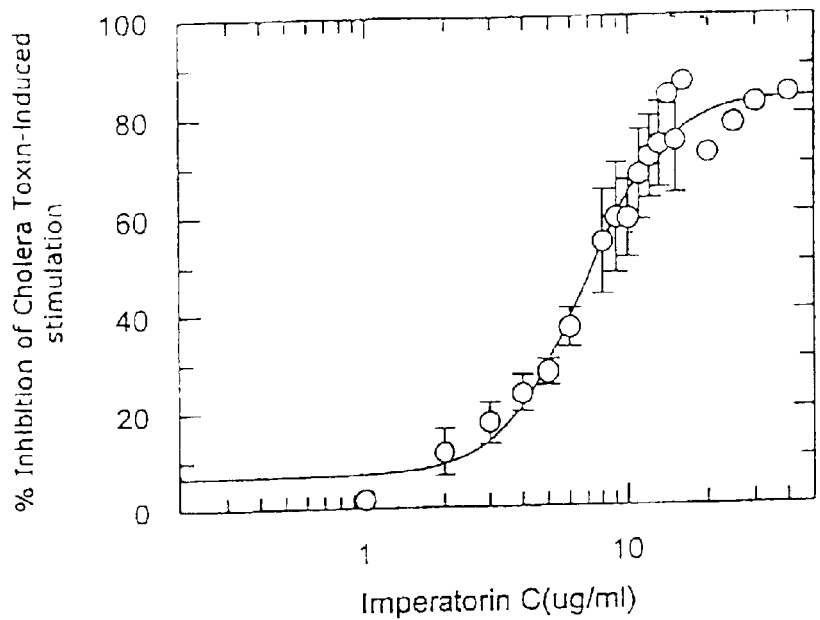
FIG. 2. Inhibition of cholera-induced and forskolin-induced chloride ion secretion by imperatorin.
Figure 2:
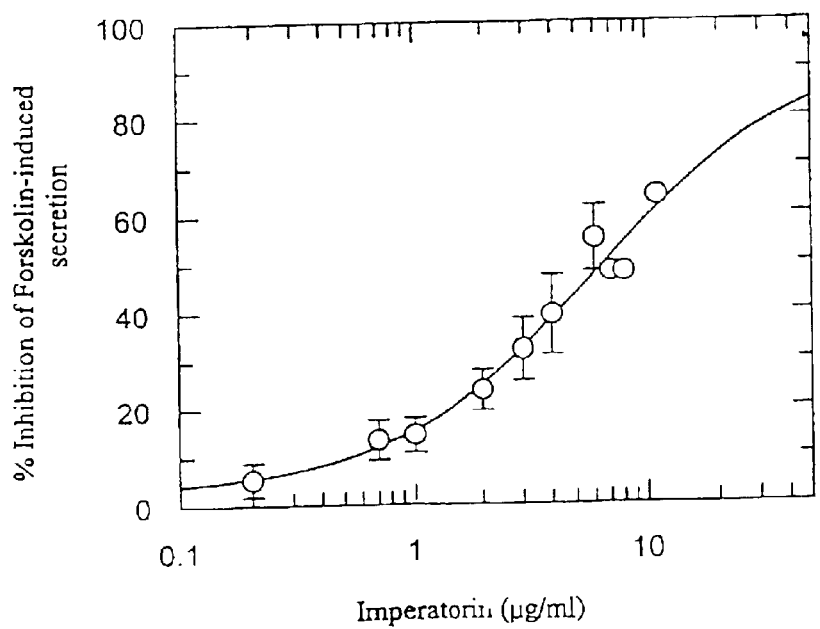
Figure 3:
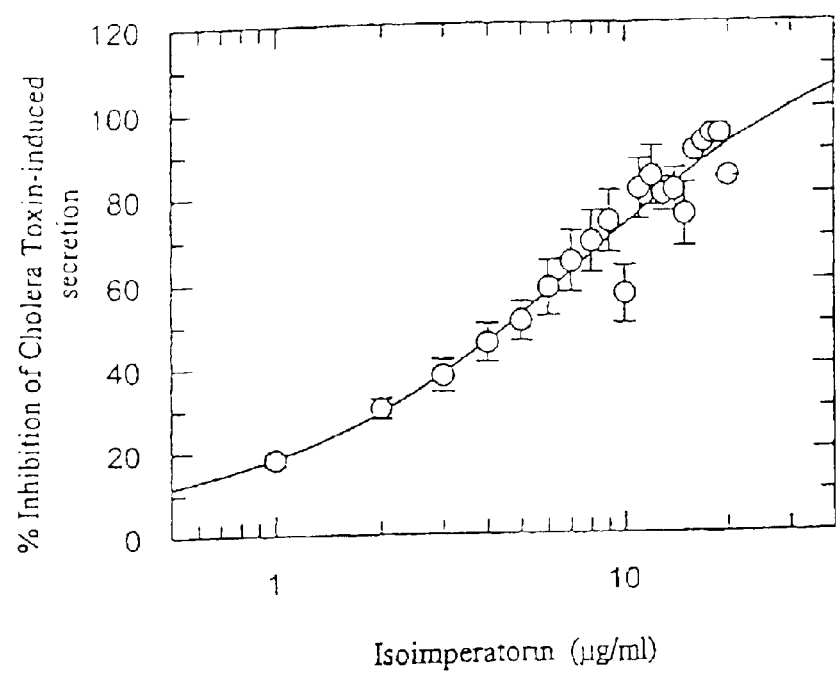
FIG. 3. Inhibition of cholera-induced and forskolin-induced chloride ion secretion by isoimperatorin.
Figure 3:
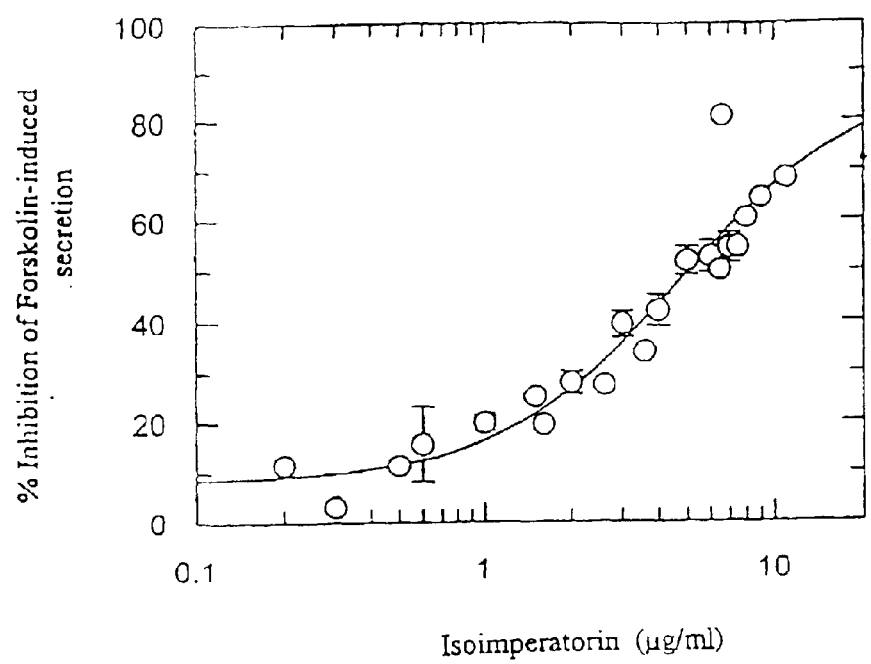

The example illustrates the inhibitory effect of active components of BJW on cAMP-activated Cl⁻ secretion in a Cl⁻-secreting human colonic cell line, $T_{84}$. Since activation of adenylate cyclase leading to elevation of cAMP is the underlying mechanism for many secretory diarrheas including $PGE_2$-induced and cholera toxin-induced diarrhea, both Cl⁻ secretion across the monolayers of $T_{84}$ cells induced by an adenylate cyclase activator, forskolin (10 µM), as well as that induced by cholera toxin, were examined. Respective concentration-response curves for the inhibitory effect of honokiol, imperatorin and isoimperatorin on forskolin-induced and cholera toxin-induced secretion are shown in FIGS. 1, 2, and 3, with similar $IC_{50}$s (4–7 µg/ml). These results demonstrate that the said active compounds act similarly to inhibit cAMP-activated Cl⁻ secretion.

The following examples illustrate the effect of BJW on other experimentally induced models of diarrhea.

Example 3

Figure 4:
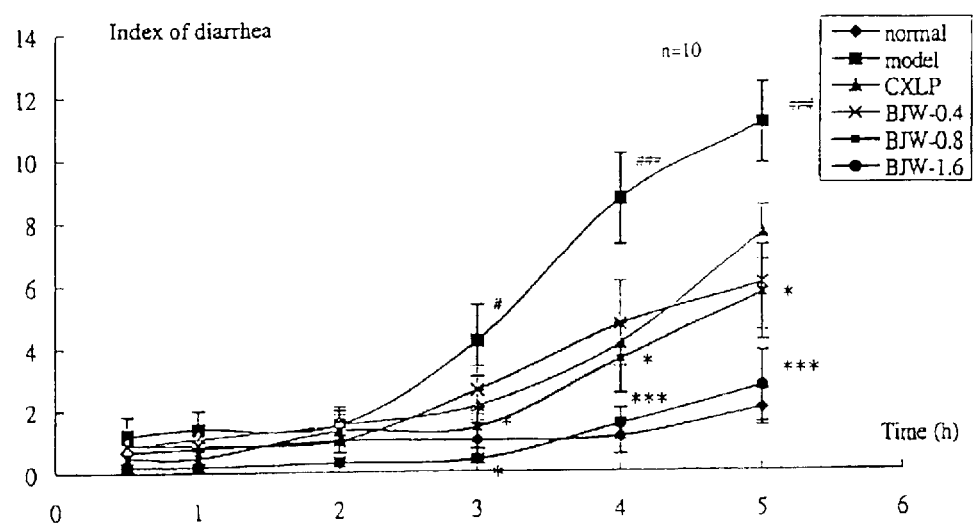
FIG. 4. Inhibition of magnesium-sulfate induced diarrhea by BJW.

This example illustrates the effect of BJW on magnesium sulfate-induced diarrhea in rats. Different doses of BJW were tested and the results are shown in FIG. 4. A potent inhibitory effect on magnesium sulfate-induced diarrhea was obtained at 1.6 g/kg (2× recommended human dosage). This is more potent than another Chinese medicine-based antidiarrheal agent, Chun Xin Lian, administered at 0.25 g/kg (10× recommended human dosage). Since the mechanisms underlying magnesium sulfate-induced diarrhea are multiple, including increased fluid volume due to increased osmotic pressure, stimulation of motility as well as secretion, complete inhibition of this diarrhea model by BJW indicates that BJW and its components can also act on mechanisms other than secretion.

Example 4

This example illustrates the effect of BJW on DaHuang-induced diarrhea in rats. DaHuang is a well known Chinese medicine for chronically inducing diarrhea, by stimulating intestinal motility and inhibiting $Na^+$ and fluid absorption. This model appears to mimic chronic diarrhea, as the animals lose weight and have a reduced body temperature. The Dahuang solution (8 mL/kg) was administered to groups of 10 rats once daily for 10 days. Test drugs or vehicle (6 mL/kg, i.g.) were administered on day 8 and measurements were performed on day 11. The results are shown in Table 2. BJW produces an inhibitory effect in a dose-dependent manner. Although the effect of BJW on this diarrhea model is less potent than that on other diarrhea models, it is more effective than another Chinese medicine-based antidiarrhea agent, CXL.

TABLE 2

Effect of BJW on Dahuang-induced diarrhea

| Group | dose (g/kg) | Intestinal transit (g) | Inhibition of diarrhea (%) |
|---|---|---|---|
| Normal | vehicle | 9.1 ± 1.0 | |
| Model | vehicle | 17.7 ± 1.9### | |
| BJW | 0.4 | 14.5 ± 1.3 | 37 |
| BJW | 0.8 | 12.1 ± 1.3* | 58 |
| BJW | 1.6 | 11.7 ± 1.3* | 70 |
| CXLP | 0.25 | 15.2 ± 1.5 | 29 |

$p < 0.01$ compared with normal group
*<0.05, compared with model group
% Inhibition of diarrhea = $(ID_{model} - ID_{test})/(ID_{model} - ID_{normal}) \times 100\%$

Example 5

Figure 5:
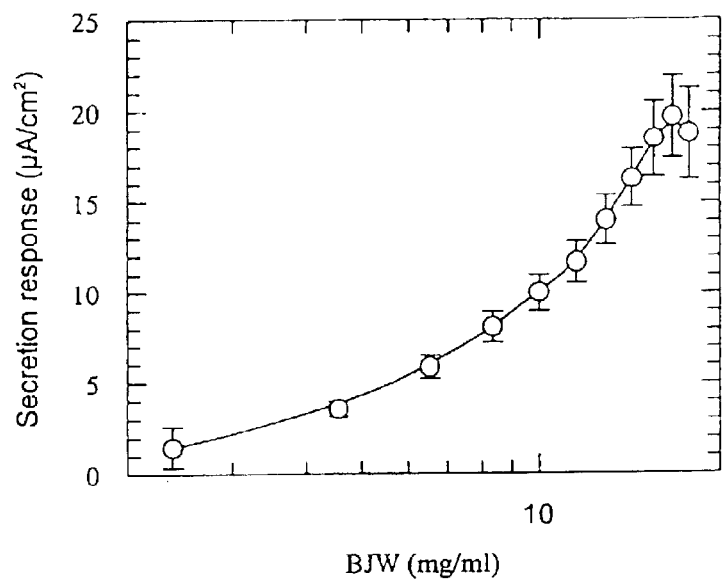
FIG. 5. Stimulation of chloride ion secretion by BJW and *Magnolia officinalis*.
Figure 5:
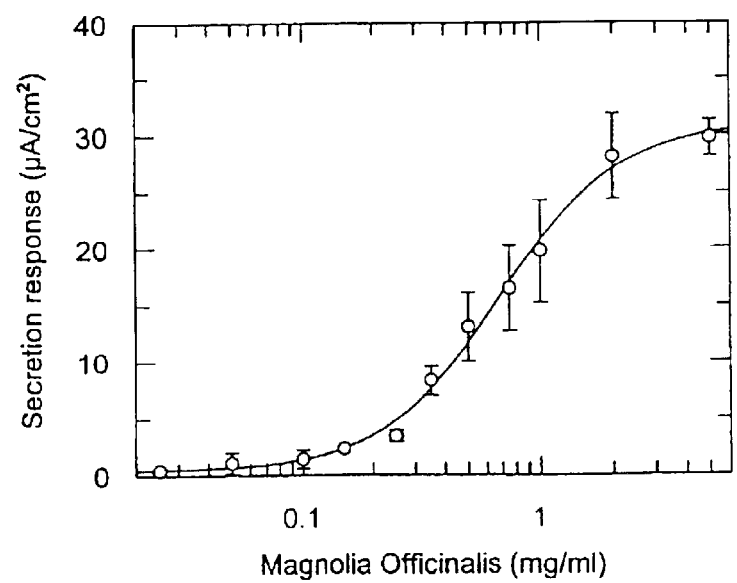

This example illustrates the stimulatory effect of BJW and its active ingredients on $Cl^-$ and fluid secretion in human colonic cells. In the absence of other stimuli, BJW and *Magnolia Officinalis*, from which magnolol and honokiol are derived, stimulated $Cl^-$ secretion (FIG. 5), thus indicating the potential of BJW and its active ingredients as laxatives.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for treating diarrhea, the method comprising the step of administering to a subject a therapeutically effective amount of a composition consisting essentially of one, two, or three members selected from the group consisting of: magnolol, honokiol, imperatorin, and isoimperatorin; and a physiologically acceptable carrier.

2. The method of claim 1, wherein said composition consists essentially of magnolol and a physiologically acceptable carrier.

3. The method of claim 1, wherein said composition consists essentially of honokiol and a physiologically acceptable carrier.

4. The method of claim 1, wherein said composition consists essentially of imperatorin and a physiologically acceptable carrier.

5. The method of claim 1, wherein said composition consists essentially of isoimperatorin and a physiologically acceptable carrier.

6. The method of claim 1, wherein said composition consists essentially of magnolol, honokiol, and a physiologically acceptable carrier.

7. The method of claim 1, wherein said composition consists essentially of magnolol, imperatorin, and a physiologically acceptable carrier.

8. The method of claim 1, wherein said composition consists essentially of magnolol, isoimperatorin, and a physiologically acceptable carrier.

9. The method of claim 1, wherein said composition consists essentially of magnolol, honokiol, imperatorin, isoimperatorin, and a physiologically acceptable carrier.

10. A method according to claim 1, wherein said subject is a human.

11. A method according to claim 1, wherein said diarrhea is caused by increased chloride ion and water secretion.

12. A method according to claim 1, wherein said diarrhea is caused by a virus, a bacterium, a neuroendocrine tumor, a parasite, or HIV.

13. A method according to claim 12, wherein said diarrhea is caused by cholera toxin.

14. A method for treating diarrhea, the method comprising the step of administering to a subject a therapeutically effective amount of a composition consisting of: magnolol, honokiol, imperatorin, and isoimperatorin; and a physiologically acceptable carrier.

15. A method according to claim 14, wherein said subject is a human.

16. A method according to claim 14, wherein said diarrhea is caused by increased chloride ion and water secretion.

17. A method according to claim 14, wherein said diarrhea is caused by a virus, a bacterium, a neuroendocrine tumor, a parasite, or HIV.

18. A method according to claim 17, wherein said diarrhea is caused by cholera toxin.

19. A method for treating constipation, the method comprising the step of administering to a subject a therapeutically effective amount of a composition consisting essentially of any one, two, or three members selected from the group consisting of: magnolol, honokiol, imperatorin, and isoimperatorin; and a physiologically acceptable carrier.

20. The method of claim 19, wherein said composition consists essentially of magnolol and a physiologically acceptable carrier.

21. The method of claim 19, wherein said composition consists essentially of honokiol and a physiologically acceptable carrier.

22. The method of claim 19, wherein said composition consists essentially of imperatorin and a physiologically acceptable carrier.

23. The method of claim 19, wherein said composition consists essentially of isoimperatorin and a physiologically acceptable carrier.

24. The method of claim 19, wherein said composition consists essentially of magnolol, honokiol, and a physiologically acceptable carrier.

25. The method of claim 19, wherein said composition consists essentially of magnolol, imperatorin, and a physiologically acceptable carrier.

26. The method of claim 19, wherein said composition consists essentially of magnolol, isoimperatorin, and a physiologically acceptable carrier.

27. The method of claim 19, wherein said composition consists essentially of magnolol, honokiol, imperatorin, isoimperatorin and a physiologically acceptable carrier.

28. The method of claim 19, wherein said subject is a human.

29. The method of claim 19, wherein said constipation is caused by decreased chloride ion and water secretion.

30. The method of claim 19, wherein said constipation is a symptom or side effect of a gastrointestinal carcinoma, Behect's disease, a primary or secondary enteric neuropathy, gastrointestinal dysfunction in Parkinson's disease, irritable bowel syndrome, chronic constipation, bowel dysfunction in Hirschsprung's disease, slow transit constipation, gastrointestinal dysfunction in Alzheimer's disease, or chronic opioid treatment.

31. A method for treating constipation, the method comprising the step of administering to a subject a therapeutically effective amount of a composition consisting of: magnolol, honokiol, imperatorin, and isoimperatorin; and a physiologically acceptable carrier.

32. The method of claim 31, wherein said subject is a human.

33. The method of claim 31, wherein said constipation is caused by decreased chloride ion and water secretion.

34. The method of claim 31, wherein said constipation is a symptom or side effect of a gastrointestinal carcinoma, Behect's disease, a primary or secondary enteric neuropathy, gastrointestinal dysfunction in Parkinson's disease, irritable bowel syndrome, chronic constipation, bowel dysfunction in Hirschsprung's disease, slow transit constipation, gastrointestinal dysfunction in Alzheimer's disease, or chronic opioid treatment.

* * * * *